(12) United States Patent
Bien et al.

(10) Patent No.: US 11,398,671 B2
(45) Date of Patent: Jul. 26, 2022

(54) BIOSENSOR USING ARRAY ANTENNA

(71) Applicant: UNIST (ULSAN NATIONAL INSTITUTE OF SCIENCE AND TECHNOLOGY), Ulsan (KR)

(72) Inventors: Franklin Don Bien, Ulsan (KR); Gang Il Byun, Ulsan (KR)

(73) Assignee: UNIST (Ulsan National Institute of Science and Technology), Ulsan (KR)

( * ) Notice: Subject to any disclaimer, the term of this patent is extended or adjusted under 35 U.S.C. 154(b) by 0 days.

(21) Appl. No.: 17/526,934

(22) Filed: Nov. 15, 2021

(65) Prior Publication Data

US 2022/0077571 A1    Mar. 10, 2022

Related U.S. Application Data

(63) Continuation of application No. PCT/KR2020/008014, filed on Jun. 19, 2020.

(30) Foreign Application Priority Data

Jun. 21, 2019 (KR) .................. 10-2019-0074031
Jun. 9, 2020  (KR) .................. 10-2020-0069613

(51) Int. Cl.
*H01Q 3/44* (2006.01)
*H01Q 1/27* (2006.01)
*H01Q 3/36* (2006.01)

(52) U.S. Cl.
CPC .............. *H01Q 1/273* (2013.01); *H01Q 3/36* (2013.01)

(58) Field of Classification Search
None
See application file for complete search history.

(56) References Cited

U.S. PATENT DOCUMENTS 11,197,612 B2 *  12/2021  Costantine .............. H01Q 7/00
2019/0104939 A1 *  4/2019  Costantine ........... H01Q 1/2291

FOREIGN PATENT DOCUMENTS

| JP | 2014-090877 A | 5/2014 | |
| JP | 2015-154930 A | 8/2015 | |
| JP | 2019-511267 A | 4/2019 | |
| KR | 10-2010-0007078 | 1/2010 | |
| KR | 10-2018-0088156 | 8/2018 | |
| WO | 2018/102435 A1 | 6/2018 | |
| WO | WO 2019/071138 | * 4/2019 | ............. A61B 5/145 |

* cited by examiner

*Primary Examiner* — Trinh V Dinh
(74) *Attorney, Agent, or Firm* — Christensen O'Connor Johnson Kindness PLLC

(57) ABSTRACT

A biosensor using an array antenna includes: at least two antenna elements that are spaced apart from each other along the lateral circumference of an object, radiate electromagnetic waves having a directivity toward the inside of the object, and receive a scattered electromagnetic field; a signal generator for generating a feed signal with a frequency sweep; a phase shifter for adjusting the phase of the feed signal and transmitting the feed signal to the at least two antenna elements; and a controller for detecting the location of a target part inside the object based on the scattered electromagnetic field received in response to the radiated electromagnetic waves by sweeping the frequency and phase of the feed signal.

15 Claims, 14 Drawing Sheets

BIOSENSOR USING ARRAY ANTENNA

CROSS-REFERENCES TO RELATED APPLICATIONS

This is a continuation of International Application No. PCT/KR2020/008014, filed Jun. 19, 2020, which claims the benefits of Korean Patent Application No. 10-2019-0074031, filed Jun. 21, 2019 and Korean Patent Application No. 10-2020-0069613, filed Jun. 9, 2020.

BACKGROUND OF INVENTION

Field of Invention

The present disclosure relates to a biosensor using an array antenna.

Description of Related Art

Recently, more and more people are suffering from so-called adult-onset diseases such as diabetes, hyper lipidemia, blood clots, etc., attributed to the westernization of dietary habits. A simple way of figuring out the seriousness of these diseases is to measure biological components in the blood. The measurement of biological components allows for detecting the amounts of various components in the blood associated with glucose, anemia, blood clots, etc., which is advantageous in that any one can find out whether the level of a particular component is in a normal range or in an abnormal range, without going to a clinic.

One of the simplest methods of biological component measurement is to inject a drop of blood drawn from a fingertip into a test strip and then perform quantitative analysis of an output signal by electrochemistry or photometry. This method is suitable for people with no expertise knowledge since the meter displays the amounts of components.

A biosensor may be used in combination with a smart device, which requires quick and accurate measurement of biometric information.

BRIEF SUMMARY OF THE INVENTION

An exemplary embodiment of the present disclosure provides a biosensor using an array antenna, including: at least two antenna elements that are spaced apart from each other along the lateral circumference of an object, radiate electromagnetic waves having a directivity toward the inside of the object, and receive a scattered electromagnetic field; a signal generator for generating a feed signal with a frequency sweep; a phase shifter for adjusting the phase of the feed signal and transmitting the feed signal to the at least two antenna elements; and a controller for detecting the location of a target part inside the object based on the scattered electromagnetic field received in response to the radiated electromagnetic waves by sweeping the frequency and phase of the feed signal.

The controller may start measuring biometric information of the target part, in response to a detection of the location of the target part.

The controller may obtain a frequency response characteristic for the scattered electromagnetic field, calculate a time delay profile from the frequency response characteristic, and determine the location of the target part based on the time delay profile.

The controller may detect a target peak from the time delay profile and determines the location of the target part based on the target peak of the time delay profile.

The controller may maintain a phase difference corresponding to the time delay profile, in response to a second peak as the target peak that has a predetermined amplitude range in a predetermined delay range.

The controller may obtain a frequency response characteristic for each phase difference by sweeping the frequency of the feed signal for each of phase differences that can be selected by the phase shifter.

The controller may determine a direction in which the target part is located with respect to the biosensor.

In response to a single-mode operation, one or more of the at least two antenna elements may radiate electromagnetic waves and the other antenna elements may receive a fringing field by the electromagnetic waves, and, in response to an array-mode operation, both of the at least two antenna elements may radiate electromagnetic waves and receive the scattered electromagnetic field.

The operation time of the single mode may be longer than the operation time of the array mode.

The operation time of the single mode and the operation time of the array mode may not overlap each other.

The controller may determine glucose level data while operating in the single mode and determine time delay-related information of the glucose level data while operating in the array mode.

A beam pattern of the electromagnetic waves radiated by the at least two antenna elements may be determined based on the phase difference adjusted by the phase shifter.

The at least two antenna elements may receive signals radiated from an internal sensor disposed inside the object, and the controller may compare the phases of the signals received by the at least two antenna elements to determine whether the internal sensor and the biosensor are in alignment.

The biosensor may further include an output unit that provides the user with guidance information for changing the wearing position of the biosensor in response to a misalignment state of the internal sensor and the biosensor, wherein the controller determines an alignment state if the signals received by the at least two antenna elements are in phase and determines the misalignment state if the signals received by the at least two antenna elements are out of phase.

The at least two antenna elements may be disposed along a curved surface corresponding to a curvature on the surface of the object.

An exemplary embodiment of the present disclosure provides a method of detecting a target part, which is performed by a biosensor, the method including: generating a feed signal with a frequency sweep, for at least two antenna elements spaced apart from each other along the lateral circumference of an object; transmitting the feed signal to the at least two antenna elements by adjusting the phase of the feed signal; radiating electromagnetic waves having a directivity toward the inside of the object in response to the feed signal and receiving a scattered electromagnetic field, by the at least two antenna elements; and detecting the location of a target part inside the object based on the scattered electromagnetic field received in response to the radiated electromagnetic waves by sweeping the frequency and phase of the feed signal.

A biosensor according to an embodiment may accurately estimate a direction in which a blood vessel is located using a scattered electromagnetic field detected in the array mode.

A biosensor according to an embodiment may radiate electromagnetic waves in a beam pattern with improved directivity toward blood vessels, thereby allowing the electromagnetic waves to penetrate to a target depth at which the blood vessel is located with minimal power.

A biosensor according to an embodiment may ensure data diversity by obtaining parameters and biometric information having different characteristics in the single mode and the array mode.

A biosensor according to an embodiment may estimate glucose levels with minimum time delay and improved accuracy by using biometric information in the single mode and biometric information in the array mode.

DETAILED DESCRIPTION OF THE INVENTION

Figure 1:
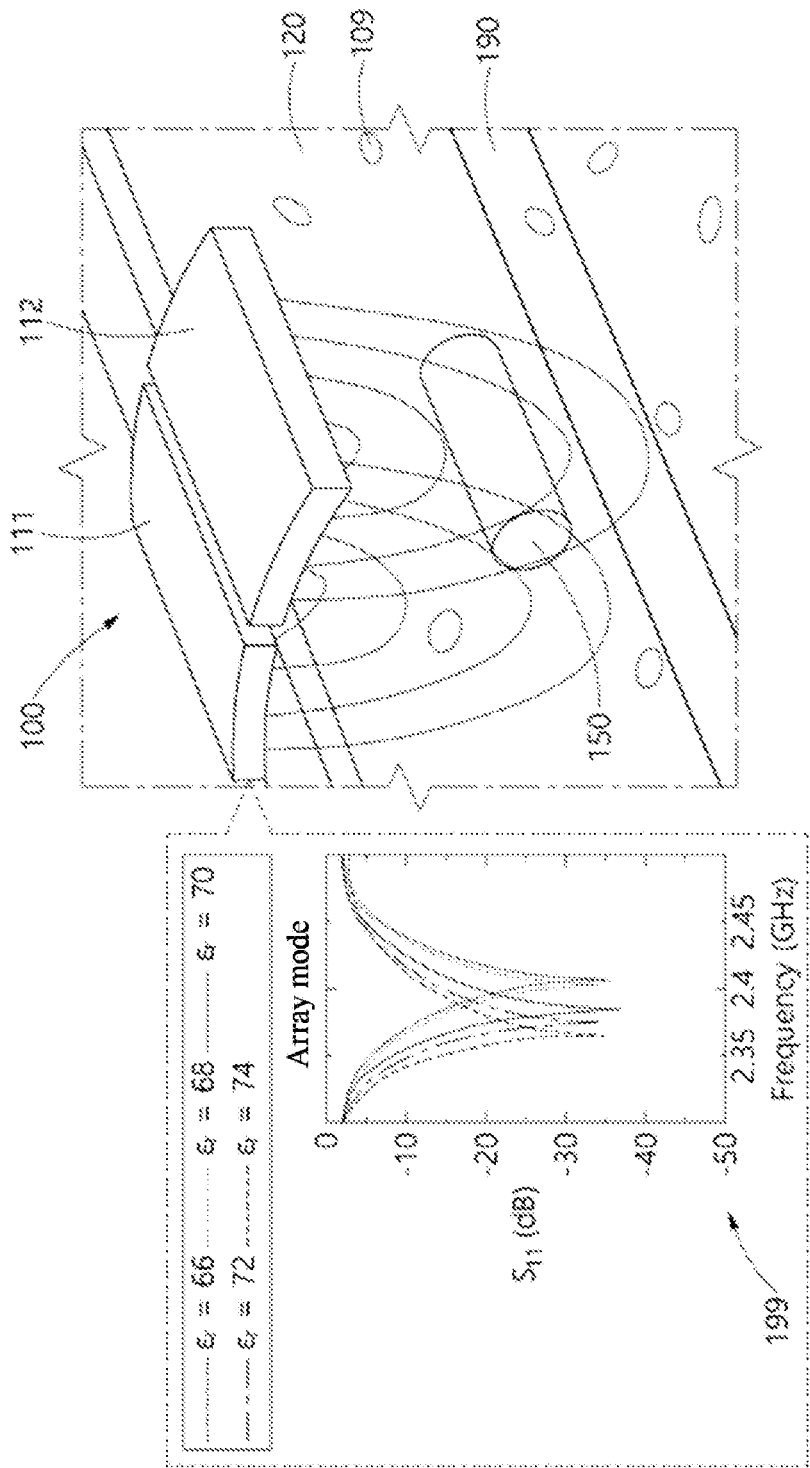
FIG. 1 illustrates a biosensor using an array antenna according to an embodiment.

Hereinafter, exemplary embodiments will be described in detail with reference to the accompanying drawings. However, since various changes may be made to the embodiments, the scope of the rights of the patent application is not limited or limited by these embodiments. It should be understood that all changes, equivalents, or substitutes to the embodiments are included in the scope of the rights.

The terms used in the example embodiments have been used for the purpose of explanation only, and the terms should not be interpreted as an intention of limiting the explanation. An expression of the singular number includes an expression of the plural number unless clearly defined otherwise in the context. In the present specification, it should be understood that a term such as "include" or "have" is used to specify existence of a feature, a number, a step, an operation, a constituent element, a part, or a combination thereof described in the specification, but it does not preclude the possibility of the existence or addition of one or more other features, numbers, steps, operations, constituent elements, parts, or combinations thereof.

Unless otherwise defined, all terms, including technical and scientific terms, used herein have the same meaning as commonly understood by one of ordinary skill in the art to which example embodiments pertain. Terms, such as those defined in commonly used dictionaries, should be interpreted as having meanings that are consistent with those in the context of the related art but are not interpreted as having ideal or excessively formal meanings unless clearly defined in the present application.

In addition, in the description with reference to the accompanying drawings, the same reference numerals are assigned to the same components regardless of the reference numerals, and redundant descriptions thereof will be omitted. In describing the embodiments, when it is determined that a detailed description of related known technologies may unnecessarily obscure the subject matter of the embodiments, the detailed description thereof will be omitted.

In describing the components of the embodiment according to the present invention, terms such as first, second, "A", "B", (a), (b), and the like may be used. These terms are merely intended to distinguish one component from another component, and the terms do not limit the nature, sequence or order of the components. When a component is described as "connected", "coupled", or "linked" to another component, this may mean the components are not only directly "connected", "coupled", or "linked", but also are indirectly "connected", "coupled", or "linked" via a third component.

A component, which has the same common function as a component included in any one example embodiment, will be described using the same name in other example embodiments. Unless otherwise stated, the description set forth in any one example embodiment may be applicable to other example embodiments, and a detailed description will be omitted in an overlapping range.

FIG. 1 illustrates a biosensor using an array antenna according to an embodiment.

A biosensing system according to an embodiment may include a biosensor 100 and an internal sensor 150.

The biosensor 100 using an array antenna may be a sensor that senses a target analyte 109 using electromagnetic waves. The target analyte 109 is a material associated with a living body, and may also be referred to as a biological material (analyte). For reference, in the present specification, the target analyte 109 has been mainly described as glucose, but is not limited thereto.

The biosensor 100 may operate in either an array mode or a single mode. The array antenna of the biosensor 100 may include at least two or more antenna elements. While the biosensor 100 operates in the array mode, each antenna element constituting the array antenna may radiate electromagnetic waves at the same time in a radiation pattern with an array factor. In this case, the antenna element may receive reflected or scattered electromagnetic waves. For example, the first antenna element 111 and the second antenna element 112 may radiate electromagnetic waves toward a subcutaneous layer 120 of an object and generate an electromagnetic field scattered by the target analyte 109 or the like. In this specification, an array-mode operation of the biosensor 100 is mainly described, and a single-mode operation of the biosensor 100 is exemplarily described with reference to FIG. 9 below. For reference, in order to maximize the distance resolution of the array antenna, antenna elements capable of operating in a wide band may be used.

According to an embodiment, the biosensor 100 may detect the location of a target part by radiating electromagnetic waves through an array antenna while operating in the array mode and receiving a scattered electromagnetic field from which the radiated electromagnetic waves are reflected. The detection of the target part will be described with reference to FIG. 7 below. In addition, while operating in the array mode, the biosensor 100 may radiate electromagnetic waves toward the target part and determine parameters associated with the target analyte 109 based on the electromagnetic field scattered with respect to the target part.

In the present specification, the parameters may represent circuit network parameters used to analyze a biosensor and/or a biosensing system. Hereinafter, for convenience of explanation, scattering parameters will be mainly described as an example, but the parameters set forth herein are not limited to them. As the parameters, for example, admittance parameters, impedance parameters, hybrid parameters, and transmission parameters may be used. For the scattering parameters, transmission coefficient and reflection coefficient may be used. For reference, the resonance frequency of the array antenna calculated from the above-described parameters may be related to the concentration of the target analyte 109, and the biosensor may predict glucose levels by detecting a change in the transmission coefficient and/or the reflection coefficient.

The resonance frequency of the array antenna may vary depending on the concentration of the target analyte 109 present around the array antenna, as described later. For example, the resonance frequency may be expressed as a capacitance component and an inductance component as shown in Equation 1 below.

$$f = \frac{1}{2\pi\sqrt{LC}} \quad \text{[Equation 1]}$$

wherein f denotes the resonance frequency of the array antenna, L denotes the inductance of the array antenna, and C denotes the capacitance of the array antenna. The capacitance C of the array antenna may be proportional to a relative dielectric constant $\varepsilon_r$ as shown in Equation 2 below.

$$C \propto \varepsilon_r \quad \text{[Equation 2]}$$

The relative dielectric constant $\varepsilon_r$ of the array antenna may be affected by the concentration of the target analyte 109 around it. For example, the array antenna operating in the array mode may radiate electromagnetic waves toward the target part, for example, the blood vessel 190. In this case, the electromagnetic waves radiated toward the blood vessel 190 may be scattered by the target analyte 109 present around it. The intensity of the scattered electromagnetic field may vary depending on the concentration of the target analyte 109, and may vary mainly depending on the concentration of the target analyte 109 in the blood vessel 190, which is the target part. Since the relative dielectric constant $\varepsilon_r$ of the array antenna varies with changes in the concentration of the target analyte 109, the resonant frequency of the array antenna also varies.

For example, FIG. 1 shows a frequency response characteristic 199 as a measurement result of scattering parameters for each relative dielectric constant of a target part in a biosensor operating in the array mode. The intensity of the scattered electromagnetic field may correspond to a reflection coefficient $S_{11}$ in the first antenna element. The biosensor may obtain a frequency response characteristic 199 by measuring the reflection coefficient $S_{11}$ within a frequency range. At the reflection coefficient $S_{11}$, a frequency representing the lowest reflection coefficient within a frequency range may be a resonance frequency. As shown in FIG. 1, the relative dielectric constant of the array antenna may decrease with increasing relative dielectric constant $\varepsilon_r$. For reference, the frequency range shown in FIG. 1 is illustrated to include 2.4 GHz, but is not limited thereto and may vary according to design.

Accordingly, the biosensor 100 according to an exemplary embodiment may directly determine biometric information about the target analyte 109 in the blood vessel 190 based on the resonance frequency of the array antenna. For example, the biosensor 100 may determine a concentration value indicated by the measured resonance frequency measured at the time of measurement, from a mapping table (e.g., a look-up table (LUT)) to which the concentration value (e.g., blood glucose level) of a target analyte corresponding to each resonance frequency is mapped. However, the determination of biometric information is not limited to this but may vary according to design.

In the present specification, the biometric information is information related to a biological component of a subject, and may include, for example, a concentration, value, etc., of an analyte, and information related to a time delay between a change in glucose level in interstitial fluid and a change in glucose level in blood vessels. If the analyte is glucose, the biometric information may include a glucose level.

The internal sensor 150 may be inserted and/or implanted in the subcutaneous layer under the skin 191. The biosensor 100 may establish communication with the internal sensor 150 wirelessly. The internal sensor 150 implanted under the skin may monitor the blood vessel 190 and the target analyte 109 present in the subcutaneous layer 120. For example, the internal sensor 150 may include a resonator assembly in which the resonant frequency varies with changes in the concentration of the target analyte 109 around it, and additional biometric data associated with the target analyte 109 may be determined by monitoring the resonant frequency of the resonator assembly. The internal sensor 150 may obtain and collect additional biometric data corresponding to the concentration of the target analyte 109 in the body, and transmit the additional biometric data to the biosensor 100 outside the body. The additional biometric data is data related to the concentration and/or amount of the target analyte 109, and may be, for example, parameters related to a relative dielectric constant corresponding to the concentration of the analyte as described above. However, the present disclosure is not limited to this, and the biometric data may include a resonant frequency corresponding to the concentration of the analyte, a scattering parameter for calculating the resonant frequency, and a frequency response characteristic corresponding to the scattering parameter. The internal sensor 150 may transmit additional biometric data to the biosensor 100 via wireless communication. Furthermore, the biosensor 100 may wirelessly supply power from the internal sensor 150. The internal sensor 150 may monitor biometric data using wirelessly transmitted power.

Figure 2:
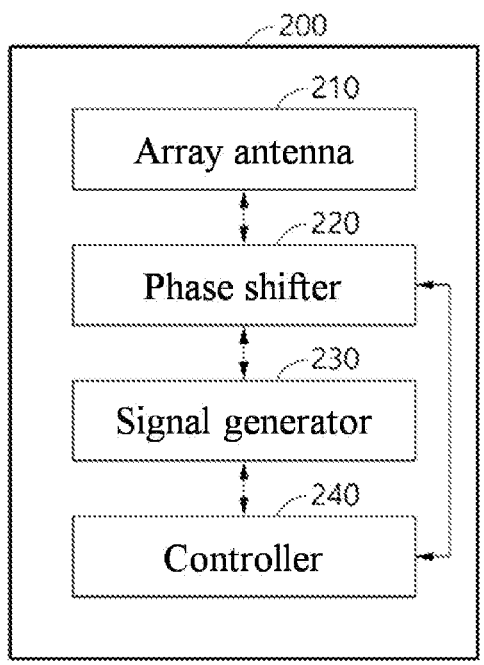
FIG. 2 is a block diagram showing a configuration of a biosensor according to an embodiment.

FIG. 2 is a block diagram showing a configuration of a biosensor according to an embodiment.

The biosensor 200 according to an embodiment may include an array antenna 210, a phase shifter 220, a signal generator 230, and a controller 240. The biosensor 200 may be attachable to the surface (e.g., skin) of the object.

The array antenna 210 may include at least two antenna elements, and may operate in either the array mode or the single mode. In the array mode, each antenna element may simultaneously radiate electromagnetic waves. In the single mode, at least one antenna element may radiate electromagnetic waves, and at least one of the other antenna elements may receive the radiated electromagnetic waves.

According to an embodiment, at least two antenna elements may be spaced apart from each other along the lateral circumference of the object. The object may be a living body and/or a part of a living body (e.g., a body part). For example, the object may be an upper arm and/or a lower arm of a person, and the antenna elements may be spaced apart from each other along the lateral circumference of the person's arm. The biosensor may also be placed on a portion of the arm corresponding to the biceps and/or triceps. In other words, the antenna elements may be spaced apart from each other along an axis (e.g., a vertical axis) crossing the target part (e.g., blood vessel) lengthwise. The antenna elements radiate electromagnetic waves having a directivity toward the inside of the object, and may receive a scattered electromagnetic field.

The phase shifter 220 may adjust the phase of the feed signal and transmit it to at least two antenna elements. The phase shifter 220 may adjust a phase difference between signals supplied to each antenna element. An exemplary configuration of the phase shifter 220 will be described with reference to FIG. 6 below.

The signal generator 230 may generate a feed signal with a frequency sweep. The signal generator 230 may include, for example, an injection locked oscillator. The signal generator 230 may generate a feed signal while sweeping a frequency within a predefined frequency range. For example, the carrier frequency of the feed signal may gradually change. The frequency range may include frequencies higher than or equal to a first frequency and lower than or equal to a second frequency, and the signal generator 230 may generate the feed signal while sequentially increasing the frequency from the first frequency to the second frequency. However, the present disclosure is not limited to this, and the signal generator 230 may generate the feed signal while sequentially decreasing the frequency from the second frequency to the first frequency.

The controller 240 may detect the location of a target part inside the object based on the scattered electromagnetic field received in response to the radiated electromagnetic waves by sweeping the frequency and phase of the feed signal.

Figure 3:
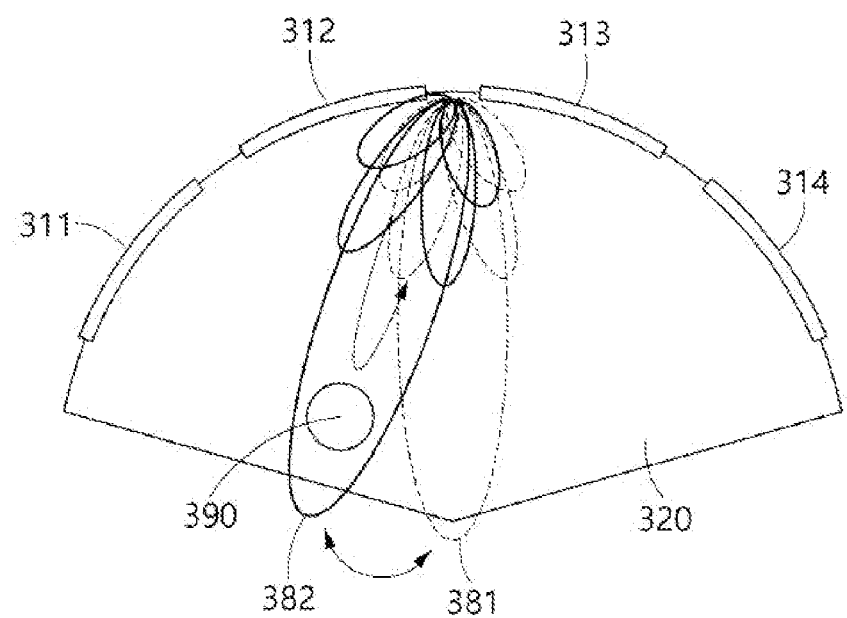
FIG. 3 is a diagram for explaining the adjustment of a beam steering angle of a biosensor according to an exemplary embodiment.

FIG. 3 is a diagram for explaining the adjustment of a beam steering angle of a biosensor according to an exemplary embodiment.

The biosensor according to an embodiment may change a beam steering angle of electromagnetic waves while radiating the electromagnetic waves into the object through a plurality of antenna elements 311, 312, 313, and 314. For example, the biosensor may change the radiation pattern of the array antenna by adjusting the intensity and phase of the feed signal to the plurality of antenna elements 311, 312, 313, and 314 according to an array factor. For example, the respective radiation patterns of the plurality of antenna elements 311, 312, 313, and 314 may overlap according to the array factor, so that electromagnetic radiation may be concentrated in a specific direction. In this array mode, the biosensor may transmit electromagnetic waves more deeply with relatively little power compared to the single mode. In addition, since electromagnetic radiation is concentrated in the direction of beam steering, the influence on the living body may be minimized. For reference, although four antenna elements 311, 312, 313, and 314 are illustrated in FIG. 3, the present invention is not limited to this.

Whenever the biosensor changes the beam steering angle, the biosensor may attempt to detect the target part in a direction corresponding to the beam steering angle with respect to the biosensor. The target part may be, for example, a blood vessel 390. The relative dielectric constant of the target part may be, for example, 80 or higher, and the relative dielectric constant of the subcutaneous layer 320 may be approximately 5. Since the relative dielectric constant of the target part is higher than the relative dielectric constant of the subcutaneous layer 320, when electromagnetic waves are radiated toward the target part, strong reflected waves may cause scattering. For example, when electromagnetic waves are radiated at a first steering angle 381, the intensity of the scattered electromagnetic field may be low. When the electromagnetic waves are radiated at a second steering angle 382, the intensity of the scattered electromagnetic field may be high due to a sharp difference in relative dielectric constant between the target part 390 and the subcutaneous layer 320. Accordingly, the biosensor may monitor the scattered electromagnetic field for each individual beam steering angle, thereby determining whether the target part is present at a position corresponding to the corresponding beam steering angle. The detection of the target part will be described in detail with reference to FIG. 7 below.

According to an embodiment, a surface on which the plurality of antenna elements 311, 312, 313, and 314 are disposed may have a curvature. The plurality of antenna elements 311, 312, 313, and 314 may be disposed along a surface (e.g., a curved surface) corresponding to a curvature on the surface of the object. For example, the plurality of antenna elements 311, 312, 313, and 314 may be disposed along a surface that fits a curved surface of an outer circumference perpendicular to the length of the object. For example, FIG. 3 is a cross-sectional view perpendicular to the longitudinal axis of the object, showing that the plurality of antenna elements 311, 312, 313, and 314 are arranged in close contact with the surface of the object. The plurality of antenna elements 311, 312, 313, and 314 may be held in a housing individually and/or collectively, and in this case, a surface of the housing contacting the object may have a curvature. Similarly, the surface of the housing contacting the object may have a curvature the same as or similar to the curvature of the outer circumference perpendicular to the length of the object. In FIG. 1, the surface on which the antenna elements are disposed is shown to have a curved shape. Accordingly, the antenna element and the housing holding the antenna elements are in close contact with the surface (e.g., skin) of the object, thereby minimizing air gaps and therefore minimizing radiation loss.

Figure 4:
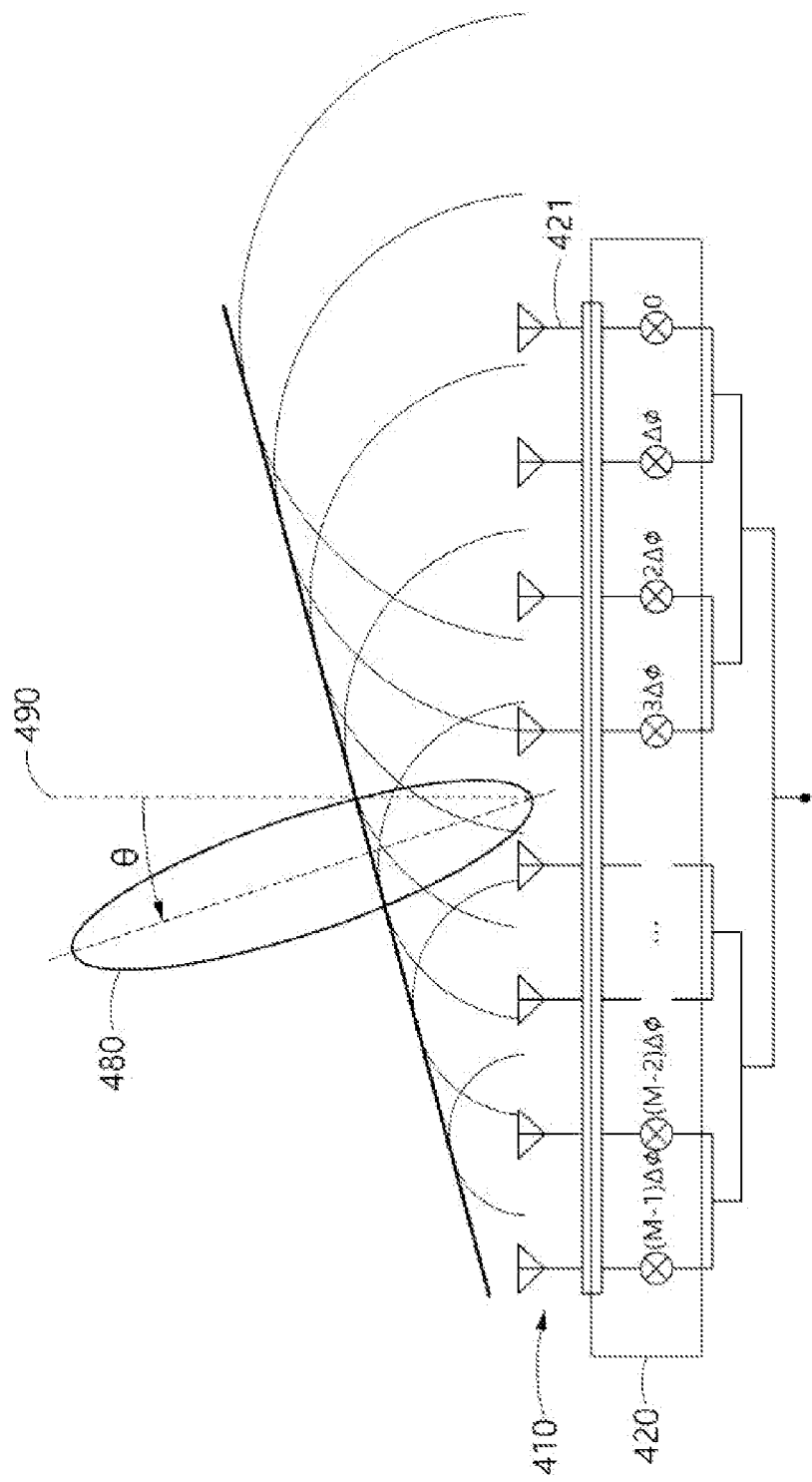
FIG. 4 illustrates a relationship between a phase difference between feed signals supplied to a plurality of antenna elements and a beam steering angle of an array antenna according to an exemplary embodiment.

FIG. 4 illustrates a relationship between a phase difference between feed signals supplied to a plurality of antenna elements and a beam steering angle of an array antenna according to an exemplary embodiment.

The array antenna 410 may include M antenna elements, where M may be an integer of 2 or more. The beam steering angle θ at the array antenna 410 of the biosensor may be an angle with respect to the central axis 490 of the steering range of the array antenna 410. The phase difference ΔØ between the antenna elements relative to the beam steering angle θ may be expressed as in Equation 3 below.

$$\Delta\phi = kd\sin\theta = \frac{2\pi}{\lambda}d\sin\theta \qquad \text{[Equation 3]}$$

wherein λ denotes the wavelength of a radiated electromagnetic wave, d denotes the distance between the antenna elements, and k denotes a constant determined by the above-described wavelength and distance. The biosensor may supply a feed signal to each antenna element with the phase difference ΔØ between the individual antenna elements, in order to radiate electromagnetic waves to a radiation pattern 480 toward the beam steering angle θ with respect to the central axis 490. For example, the phase shifter 420 may supply a feed signal to a second antenna element after a delay of ΔØ, to a third antenna element after a delay of 2ΔØ, and to an Mth antenna element after a delay of (M−1)ΔØ, with respect to the feed signal supplied to the first antenna element. Although described later in FIG. 7 below, a plurality of phase differences may be determined for each beam steering angle defined by an angle resolution, and the biosensor may sequentially select a plurality of phase differences and supply a feed signal to the antenna elements with the selected phase differences.

Figure 5:
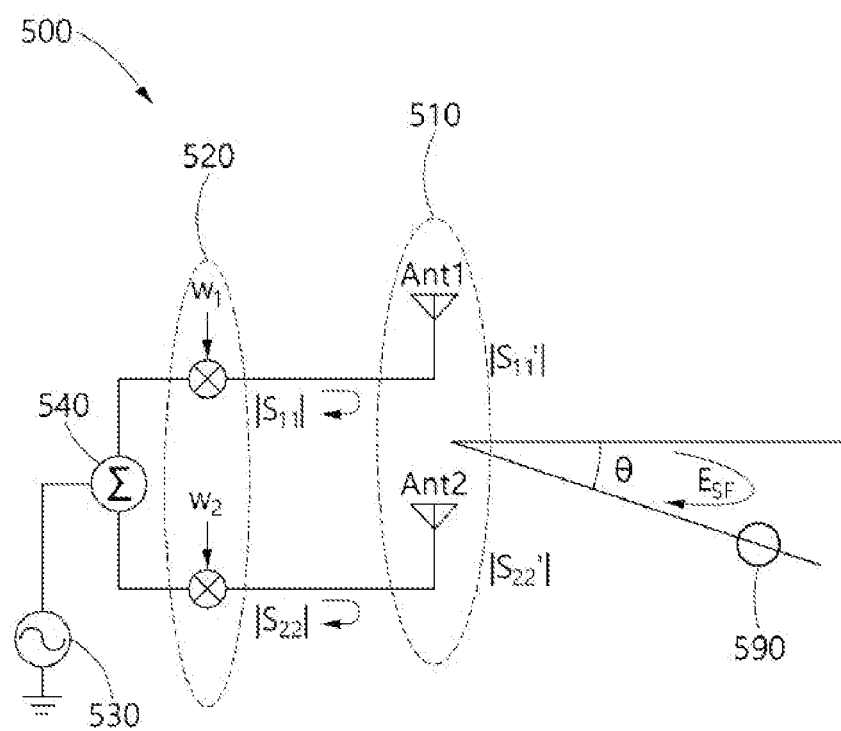
FIG. 5 illustrates a circuit diagram of a biosensor operating in an array mode according to an embodiment.

FIG. 5 illustrates a circuit diagram of a biosensor operating in an array mode according to an embodiment.

The biosensor 500 may include an array antenna 510, a phase shifter 520, a signal integrator 540, and a signal generator 530. The array antenna 510 may include, for example, a first antenna element and a second antenna element. As described above, the signal generator 530 may generate a feed signal. The phase shifter 520 may delay a feed signal by a phase corresponding to $w_1$ with respect to the first antenna element and a phase corresponding to $w_2$ with respect to the second antenna element and provide the delayed feed signal to each antenna element. The relationship between the phases is given by Equation 4 below.

$$\angle w_2 - \angle w_1 = kd\sin\theta = \Delta\phi \qquad \text{[Equation 4]}$$

By the above-described phase feeding, the first antenna element and the second antenna element may radiate electromagnetic waves toward the beam steering angle θ. At this point, when the target part 590 is present in the corresponding direction, a strong scattered electric field $E_{SF}$ may be generated. The parameters corresponding to the first antenna element and the second antenna element may be exemplified by Equations 5 and 6 below, respectively.

$$|S'_{11}| = |S_{11}| + E_{SF} \qquad \text{[Equation 5]}$$

$$|S'_{22}| = |S_{22}| + E_{SF} \qquad \text{[Equation 6]}$$

In the above Equation 5, $|S'_{11}|$ is the total reflection coefficient of the first antenna element, which may be the sum of the self reflection coefficient $|S_{11}|$ of the first antenna element and the scattered electric field $E_{SF}$. Similarly, in the above Equation 6, $|S'_{22}|$ is the total reflection coefficient of the second antenna element, which may be the sum of the self reflection coefficient $|S_{22}|$ of the second antenna element and the scattered electric field $E_{SF}$. The biosensor 500 may obtain a reflection coefficient as shown in Equation 7 below due to the phase delay caused by the phase shifter 520.

$$y = |S'_{11}| \times w_1 + |S'_{22}| \times w_2 \qquad \text{[Equation 7]}$$

The biosensor 500 may obtain signals received individually via the antenna elements of the array antenna 510 after having them passed through the phase shifter 520 and integrating them by the signal integrator 540. In the above Equation 7, y may represent a parameter (e.g., reflection coefficient) for signals that are received via the array antenna 510 and integrated. The biosensor 500 may measure an integrated parameter for a plurality of antenna elements included in the array antenna, rather than measuring parameters for individual antenna elements. The biosensor 500 may obtain a frequency response characteristic for the scattered electromagnetic field by measuring the parameters according to the above Equation 7 while sweeping the frequency of a feed signal for each beam steering angle θ.

Figure 6:
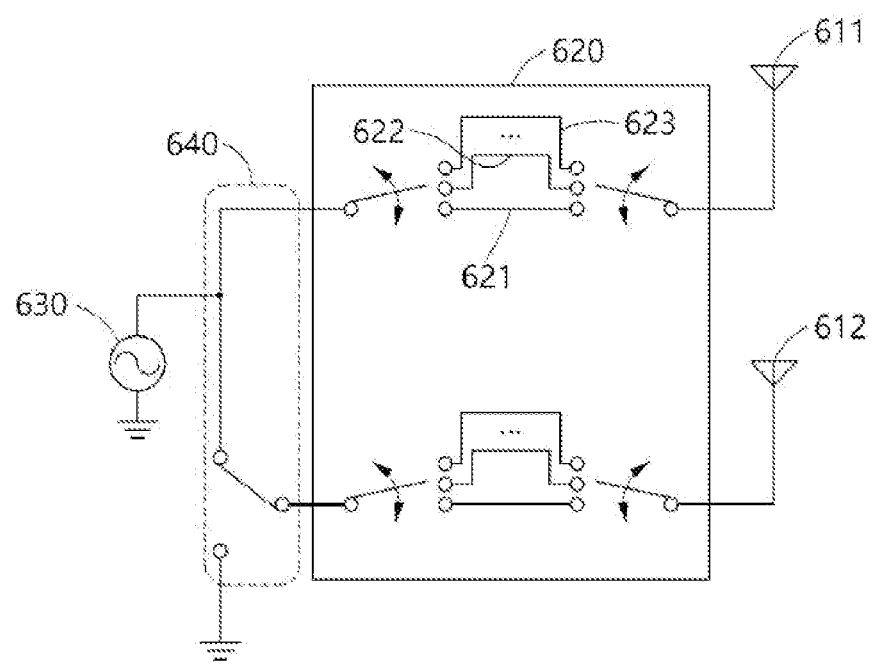
FIG. 6 illustrates an exemplary configuration of a phase shifter according to an embodiment.

FIG. 6 illustrates an exemplary configuration of a phase shifter according to an embodiment.

The phase shifter 620 may provide a phase difference between the first antenna element 611 and the second antenna element 612 by delaying a feed signal generated by a signal generator 630. For example, the phase shifter 620 may include a plurality of signal paths 621, 622, and 623 that can be selected by a phase control signal of the controller. The phase of the feed signal supplied to each antenna element from the signal generator 630 may vary depending on the length of the selected signal path from the signal generator 630 to the corresponding antenna element. Accordingly, the controller may adjust the phase delay for the corresponding antenna element by selecting the signal path of the phase shifter 620 for each antenna element through the phase control signal.

For reference, while the biosensor operates in the array mode, a path selector 640 may form a path from the signal generator 630 to each antenna element as shown in FIG. 6 in the array mode. Accordingly, in the array mode, the path selector 640 may operate as a signal integrator described above in FIG. 5. While the biosensor operates in the single mode, the path selector 640 may connect a transmission antenna (e.g., the first antenna element) and the signal generator 630 and disconnect a reception antenna (e.g., the second antenna element)) and the signal generator 630. However, the configuration of the path selector 640 is not limited to this, and may vary according to design.

Figure 7:
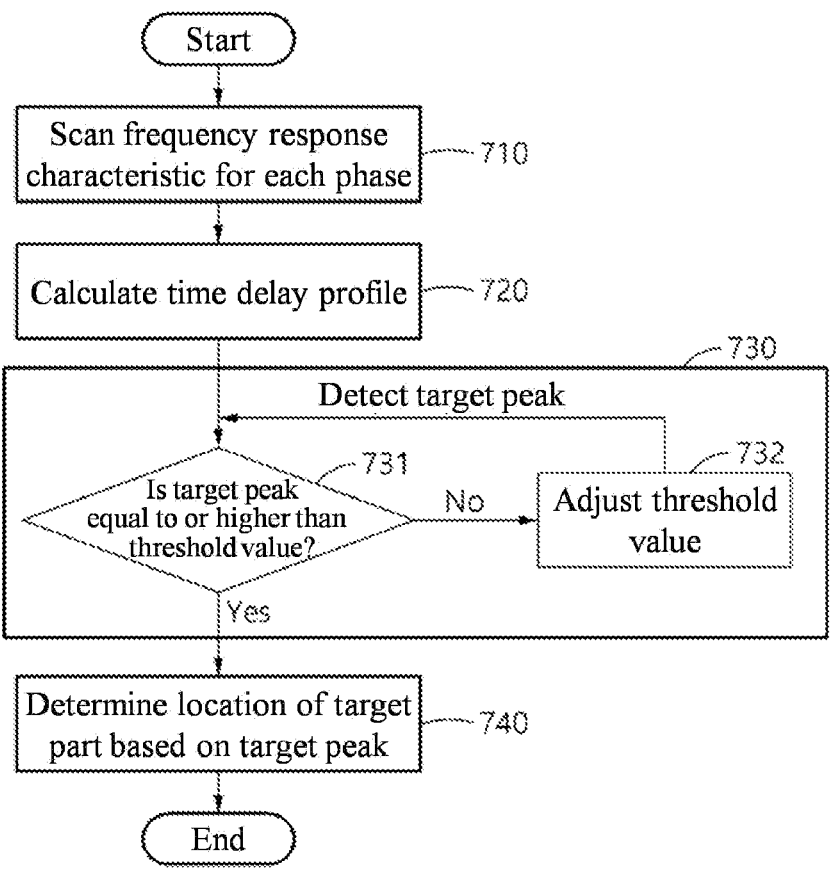
FIGS. 7 and 8 illustrate a method of detecting a target part using a biosensor according to an embodiment.
Figure 8:
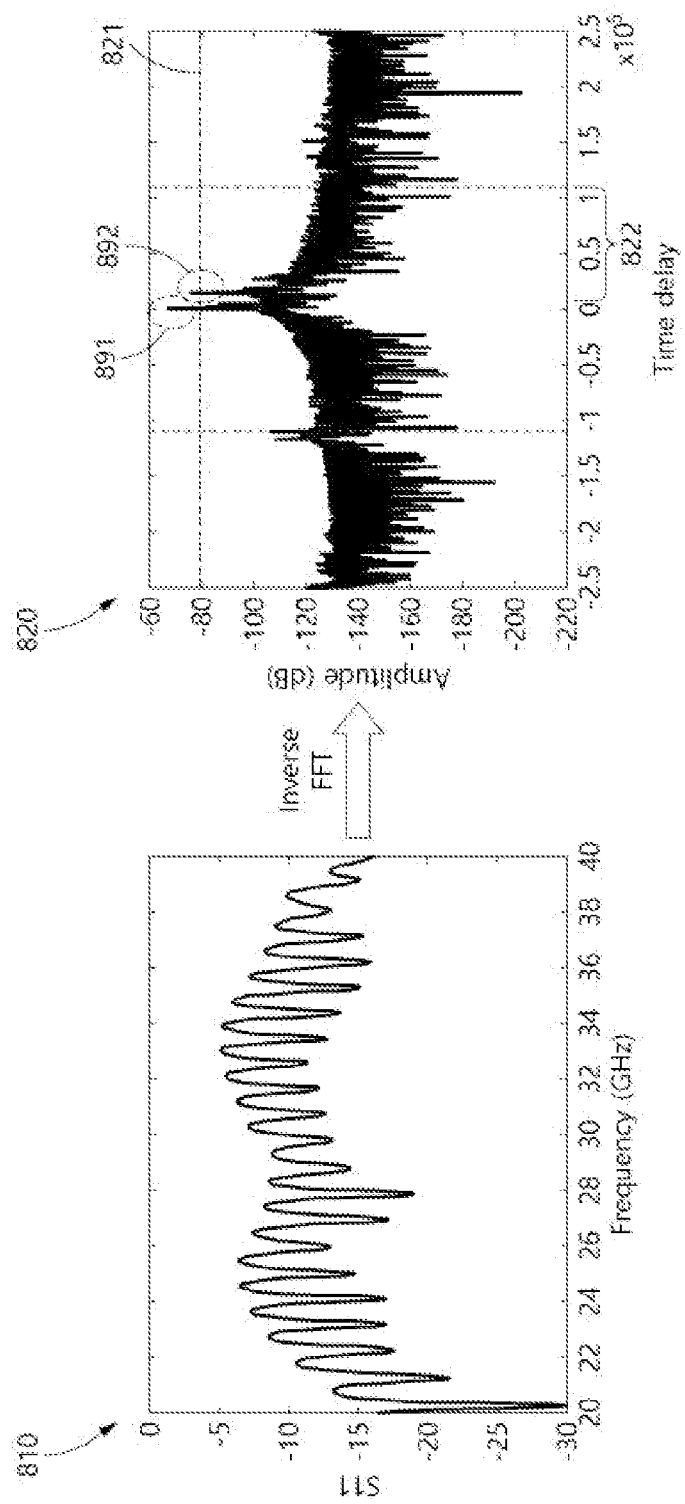

FIGS. 7 and 8 illustrate a method of detecting a target part using a biosensor according to an embodiment.

First of all, in the step 710, the biosensor may scan a frequency response characteristic 810 for each phase. According to an embodiment, the controller may obtain a frequency response characteristic 810 for each phase difference by sweeping the frequency of a feed signal for each of phase differences that can be selected by the phase shifter.

For example, beam steering angles (for example, a first angle $\theta_1$, a second angle $\theta_2$, ..., a Kth angle $\theta_K$, wherein K is an integer greater than or equal to 2) that can be selected depending on angle resolving power Δθ within the steering range of the array antenna may be predefined. The phase shifter may provide phase differences for a plurality of predefined beam steering angles. The controller may select one of the plurality of phase differences that can be selected by the phase shifter. By feeding signals to the array antenna with the selected phase difference by the phase shifter, the controller may measure a parameter regarding the scattered electromagnetic field for the electromagnetic waves radiated at the corresponding beam steering angle. The controller may obtain the frequency response characteristic for the scattered electromagnetic field for the corresponding beam steering angle by measuring the parameter while sweeping the frequency for the corresponding beam steering angle.

In step 720, the biosensor may calculate a time delay profile 820. For example, the controller may calculate a time delay profile 820 from the frequency response characteristic 810. The controller may calculate the time delay profile 820 by transforming the frequency response characteristic 810 into a time domain (e.g., the inverse of fast Fourier transform (FFT)). The frequency response characteristic 810 may be a reflection coefficient $S_{11}$ which is one of the scattering parameters, as illustrated in FIG. 8.

Subsequently, in the step 730, the biosensor may detect a target peak. The controller may determine the location of the target part based on the time delay profile 820. For example, the controller may detect a target peak from the time delay profile 820 and determine the location of the target part based on the target peak of the time delay profile 820. The controller may detect a second peak 892 as the target peak. The second peak 892 may represent a peak having the second highest intensity in descending order among the peaks detected from the time delay profile 820. A first peak 891 (e.g., a peak with the highest intensity) may be caused by self-reflection of the antenna element. The second peak 892 is generated by the scattered electromagnetic field, and a delay occurs until the electromagnetic waves are reflected and received after reaching the target part (for example, blood vessel) from the antenna element and, so it may appear later than the first peak 891.

For example, in the step 731, the controller may determine whether a target peak equal to or higher than a threshold value 821 is detected. For example, the controller may search for a point in the time delay profile 820 that exceeds the threshold value 821, except for the first peak 891. If every detected value is lower than the threshold value 821, except for the first peak 891, the controller may adjust the threshold value 821 in the step 732. For example, the controller may decrease the threshold value and perform an operation corresponding to the step 731. Thus, the controller may gradually decrease the threshold value until the second peak 892 is detected.

In the step 740, the biosensor may determine the location of the target part based on the target peak. In response to the second peak 892 as the target peak having a predetermined amplitude range in a predetermined delay range 822, the controller may determine that the target part is present at the beam steering angle corresponding to the time delay profile 820 from which the target peak is detected. In light of the depth from the skin to the blood vessel, the second peak 892 for the blood vessel may be generated within the delay range and within the amplitude range. Accordingly, the controller may exclude peaks outside the delay range 822 or the amplitude range when determining the target part. The controller may determine the direction in which the target part is located with respect to the biosensor.

The controller according to an embodiment may maintain a phase difference corresponding to the time delay profile 820 from which the target part is detected for at least two antenna elements, in response to a determination of the direction in which the target part is located. As described above, a beam pattern of the electromagnetic waves radiated by the at least two antenna elements may be determined based on the phase difference adjusted by the phase shifter. Accordingly, the biosensor may form and maintain the beam pattern of the array antenna in the direction facing the target part.

In response to a detection of the location of the target part, the controller may start measuring biometric information on the target part. For example, the controller may measure biometric information such as glucose levels in a blood vessel and/or information related to a time delay between a change in glucose level in interstitial fluid and a change in glucose level in blood vessels. The measurement of glucose levels in blood vessels was described above with reference to FIG. 1, and the time-delay related information will be described with reference to FIG. 14 below.

For reference, FIG. 7 illustrates an example in which the controller obtains the frequency response characteristic 810 for one steering angle and performs the other operations and restarts from the step 710 by changing the beam steering angle if the location of the target part is not detected. However, the present disclosure is not limited to this example, and the controller may obtain the frequency response characteristic 810 for all beam steering angles while sequentially changing the beam steering angle and perform the other operations (for example, 720 to 740).

Figure 9:
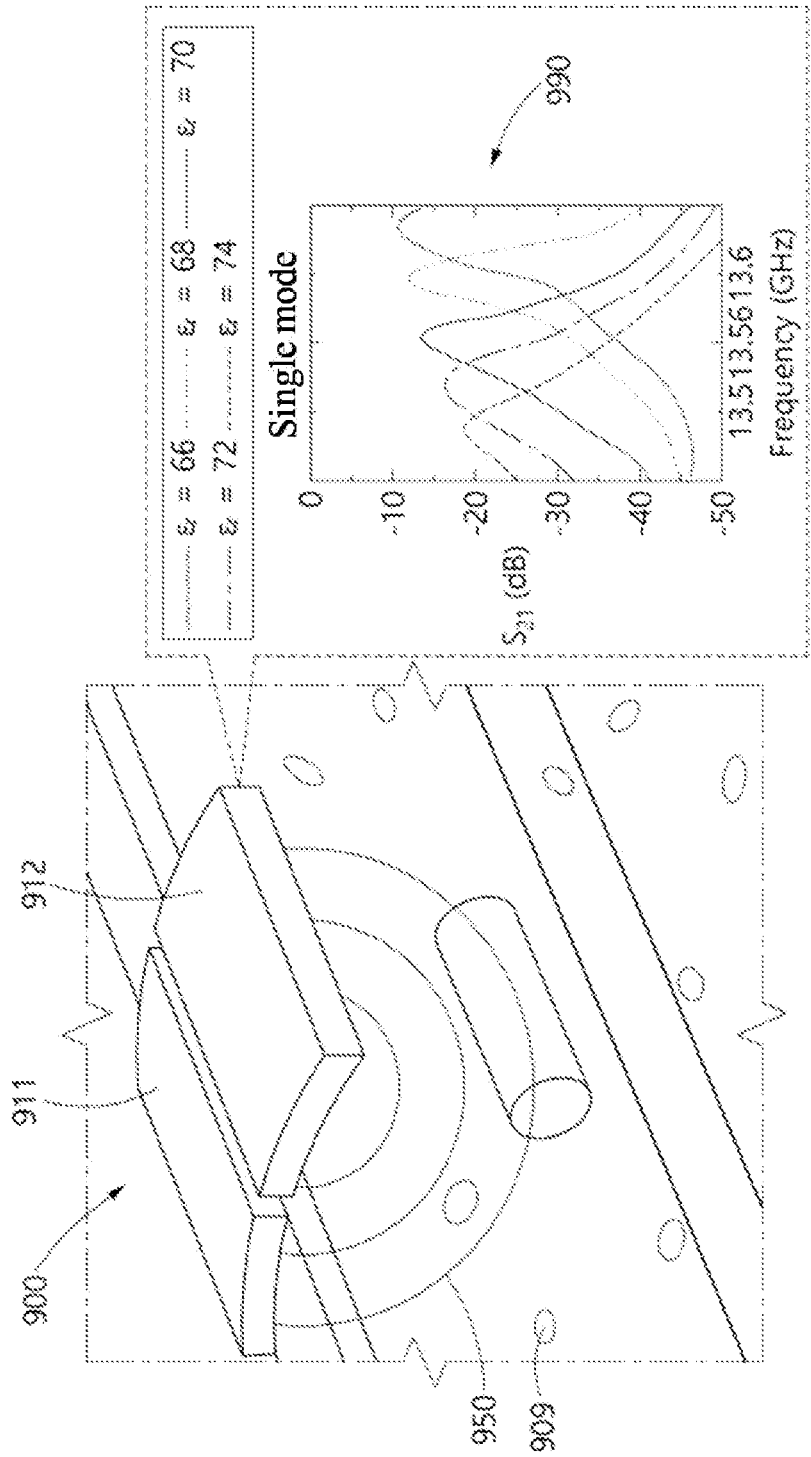
FIGS. 9 and 10 illustrate a biosensor operating in a single mode according to an embodiment.
Figure 10:
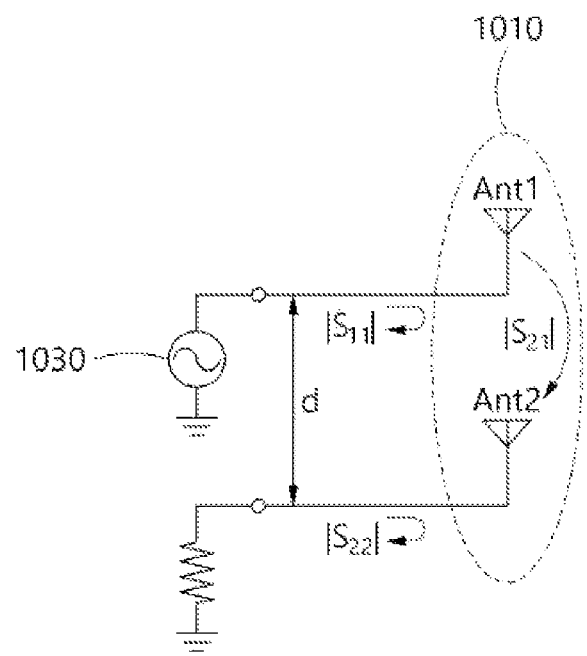

FIGS. 9 and 10 illustrate a biosensor operating in a single mode according to an embodiment.

At least two antenna elements 911 and 912 of the biosensor 900 may operate in an array mode or a single mode. As described above, in response to an array-mode operation, both of the at least two antenna elements 911 and 912 may radiate electromagnetic waves and receive a scattered electromagnetic field. In FIGS. 9 and 10, a single-mode operation will be described.

In response to a single-mode operation, one or more of the at least two antenna elements 911 and 912 may radiate electromagnetic waves and the other antenna elements may receive a fringing field 950 by the electromagnetic waves. For example, the first antenna element 911 may radiate electromagnetic waves, and the second antenna element 912 may receive the fringing field 950. The biosensor 900 may measure a transmission coefficient 990 $S_{21}$ as a scattering parameter, based on a strength received from the second antenna element 912 relative to the strength of a signal radiated from the first antenna element 911. The transmission coefficient 990 $S_{21}$ of the biosensor 900 may represent the highest value for the resonance frequency within a specific frequency range. Similarly to the array mode, the resonant frequency of the biosensor 900 operating in the single mode may vary according to a relative dielectric constant corresponding to the concentration of a target analyte 909. For reference, the range for searching for the resonance frequency is shown to be a range including 13.56 MHz in FIG. 9, but is not limited thereto and may be vary according to design.

In an array antenna 1010 operating in the single mode, electrical paths of the first antenna element 911 and the second antenna element 912 may be separated as shown in FIG. 10. The first antenna element 911 may radiate electromagnetic waves in response to a feed signal generated by a signal generator 1030. The second antenna element 912 may receive the fringing field 950.

According to an embodiment, the operation time of the single mode may be longer than the operation time of the array mode. The operation time of the single mode and the operation time of the array mode may not overlap each other. The biosensor 900 may obtain first biometric information during the single mode and obtain second biometric information during the array mode. The first biometric information and the second biometric information may include data that is related to the same target analyte and represents different characteristics. For example, the first biometric information may include data on the concentration value of a target analyte (e.g., glucose) present in the interstitial fluid of the subcutaneous layer. The second biometric information may include data on the concentration value of a target analyte present in blood vessels. Since a change in the concentration in the blood vessels has a time delay that takes longer to affect the subcutaneous layer, the second biometric information may be more sensitive to concentration changes than the first biometric information. The first biometric information may show higher accuracy in glucose level measurement. Accordingly, the biosensor 900 may fuse the first biometric information and the second biometric information to determine a precise and accurate biometric measurement result. The fusion of the first biometric information and the second biometric information may be performed by an operation based on a Bayesian filter-based algorithm, but is not limited thereto. Characteristics of the first biometric information and the second biometric information will be described with reference to FIG. 14 below.

Figure 11:
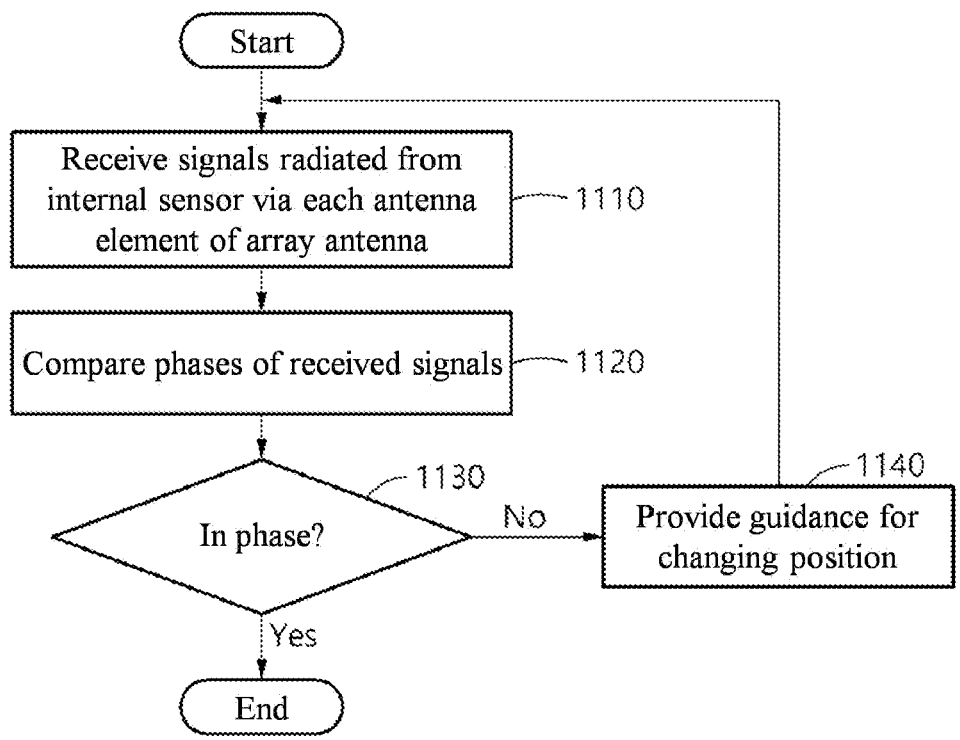
FIGS. 11 and 12 illustrate a method of providing guidance about position alignment between a biosensor and an internal sensor according to an exemplary embodiment.
Figure 12:
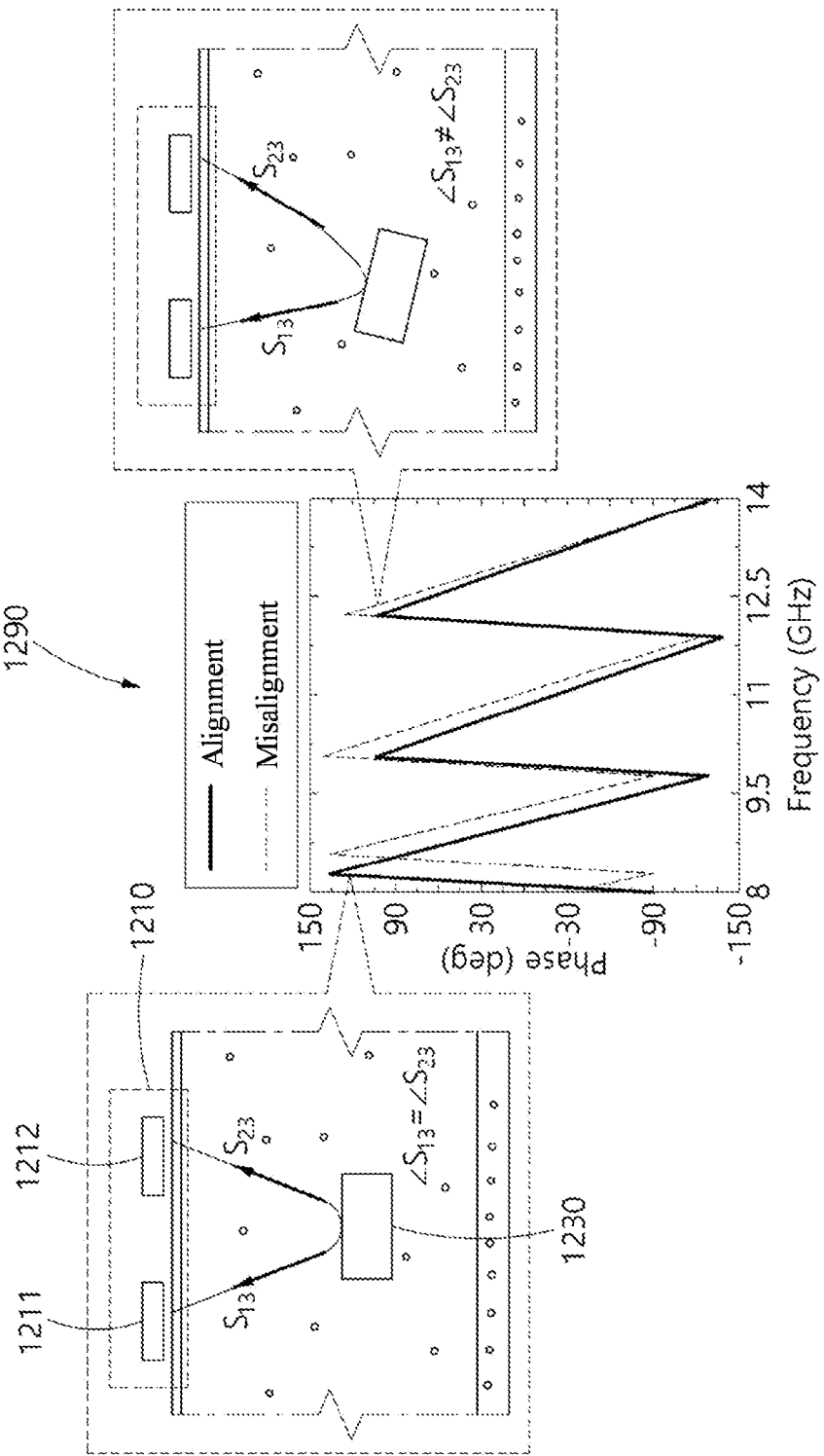

FIGS. 11 and 12 illustrate a method of providing guidance about position alignment between a biosensor and an internal sensor according to an exemplary embodiment.

First, in the step 1110, the biosensor 1210 may receive signals radiated from an internal sensor 1230 via each antenna element of an array antenna. The internal sensor 1230 may be disposed inside the object, and may radiate an electromagnetic wave signal for position alignment.

Next, in the step 1120, the biosensor 1210 may compare the phases of the received signals. For example, the controller may compare the phases of signals received by at least two antenna elements to determine whether the internal sensor 1230 and the biosensor 1210 are in alignment or not.

Subsequently, in the step 1130, the controller may determine whether the received signals are in phase. For example, in FIG. 12, it may be assumed that the array antenna of the biosensor 1210 includes a first antenna element 1211 and a second antenna element 1212, and the internal sensor 1230 includes a third antenna element. The first antenna element 1211 and the second antenna element 1212 each may receive an electromagnetic wave signal for position alignment radiated by the third antenna element. In an alignment state, the distance from the internal sensor 1230 to the first antenna element 1211 and the distance from the internal sensor 1230 to the second antenna element 1212 are equal, and therefore the received signals may be in phase. In a misalignment state, the distances from the internal sensor 1230 to each antenna element of the biosensor 1210 are different, and therefore the received signals may be out of phase. For example, as shown in a phase graph 1290, the phase in the alignment state and the phase in the misalignment state may be different, and this may lead to a deterioration in measurement accuracy. The biosensor 1210 may compare the phase of a transmission coefficient $S_{13}$ of a signal radiated from the third antenna element and received by the first antenna element 1211 and the phase of a transmission coefficient $S_{23}$ of a signal radiated by the third antenna element and received by the second antenna element 1212 to determine whether they are the same. When the signals received by the at least two antenna elements are in phase, the controller may determine the alignment state and finish the position alignment process.

In the step 1140, the controller may determine the misalignment state if the signals received by the at least two antenna elements are out of phase. The biosensor 1210 according to an embodiment may further include an output unit for outputting information related to position alignment. For example, the output unit may provide the user with guidance information for changing the wearing position of the biosensor 1210 in response to the misalignment state of the internal sensor 1230 and the biosensor 1210. The guidance information may include information about the direction of change of position on an object surface which is required to align the biosensor 1210. Accordingly, the biosensor 1210 provides guidance information for position alignment of the internal sensor 1230, thereby minimizing performance degradation due to misalignment.

Figure 13:
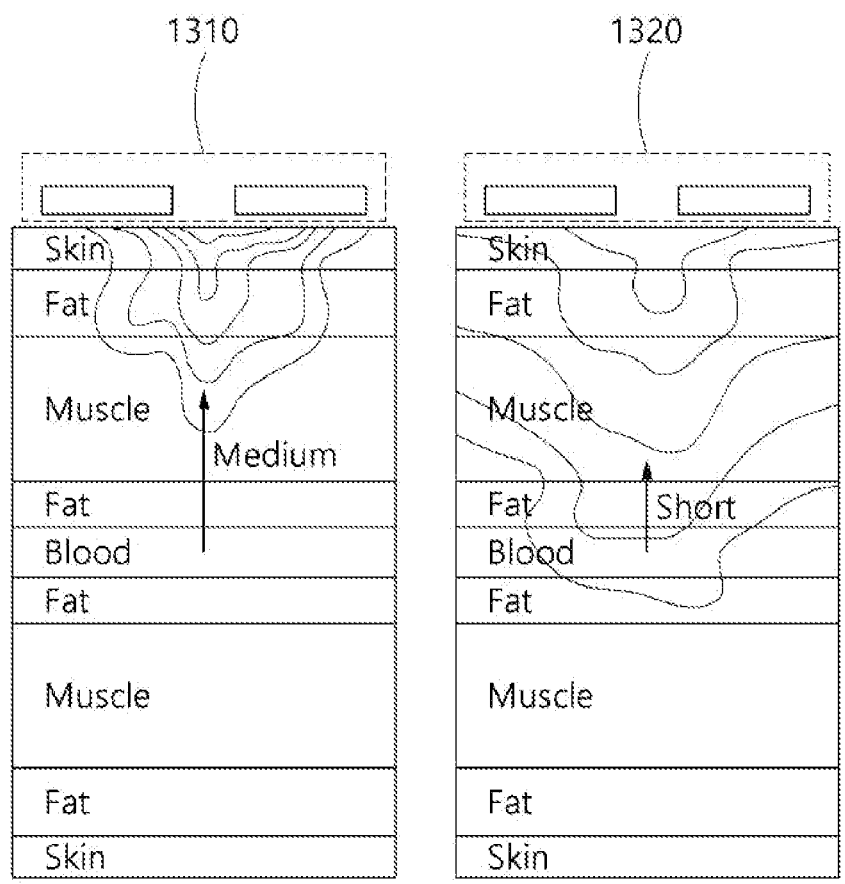
FIGS. 13 and 14 illustrate depths that can be sensed by a biosensor and its sensing results according to an embodiment.
Figure 14:
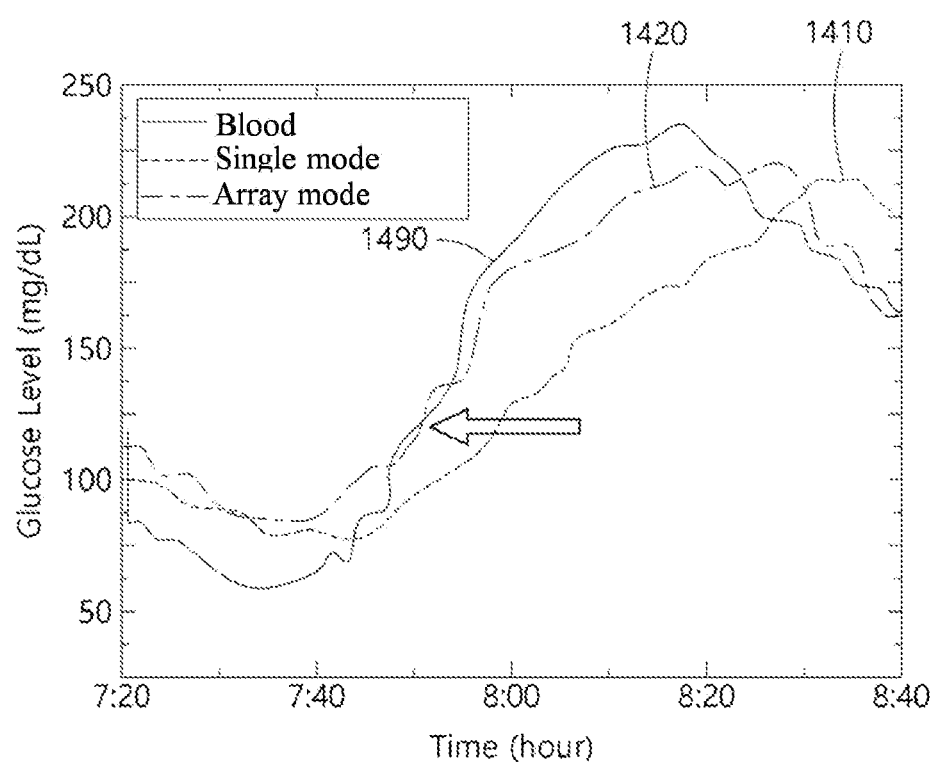

FIGS. 13 and 14 illustrate depths that can be sensed by a biosensor and its sensing results according to an embodiment.

FIG. 13 illustrates electromagnetic wave penetration depths of a biosensor 1310, operating in the single mode and a biosensor 1320, operating in the array mode. An array antenna of the biosensor 1320, operating in the array mode radiates electromagnetic waves with a beam pattern concentrated at a beam steering angle toward a target part (e.g., blood vessels in the body), thereby exhibiting a greater penetration depth compared to the single mode. The electromagnetic waves in the array mode may have improved directivity compared to the electromagnetic waves in the single mode. In the array mode, the biosensor 1320, has an improved electromagnetic wave penetration depth with minimal power, thereby minimizing electromagnetic wave loss due to the high dielectric constant of the skin layer and achieving satisfactory results when the compatibility of electromagnetic waves is tested inside the body.

In a multi-layered model of a cross-section of an arm, the biosensor 1320, in the array mode may provide electromagnetic wave transmission to as far as the blood vessels, compared to the biosensor 1310, operating in the single mode. Since the distance between a point that can be reached by electromagnetic waves radiated by the biosensor 1320, in the array mode and the blood vessels is shorter than the distance between a point that can be reached in the single mode and the blood vessels, the biosensor 1320, in the array mode may sense a rapid change in glucose level. For example, referring to FIG. 13, changes in glucose level 1420, based on biometric information sensed by the biosensor 1320, in the array mode may follow actual changes in glucose level 1490, more sensitively than changes in glucose level 1410, in the single mode.

Therefore, the biosensor determines interstitial fluid-based biometric information in the single mode and determines blood vessel-based biometric information in the array mode, and combines biometric information with different characteristics to minimize the time delay occurring in glucose level measurement and maintain the accuracy of glucose level measurement. For example, the controller of the biosensor determines glucose level data as first biometric information while operating in the single mode, and determines time delay-related information of the glucose level data as second biometric information while operating in the array mode. The controller may calculate a difference (e.g., time delay-related information) between a point in time when the interstitial fluid-based glucose level starts to change, estimated in the single mode, and a point in time when the blood vessel-based glucose level starts to change, estimated in the array mode. Thereafter, upon detecting a change in blood vessel-based glucose level estimated in the array mode at a certain point in time, the controller may accurately and quickly estimate the glucose level for that point in time by using the interstitial fluid-based glucose levels and time delay-related information that was recorded previously.

The biosensor according to an embodiment may maintain accuracy by preventing a change in performance due to an external environment. In addition, the biosensor may ensure data diversity by collecting biometric information of interstitial fluid-based characteristics and blood vessel-based characteristics and collecting information from the internal sensor as well. For example, the biosensor is able to accurately monitor glucose levels in real time by applying a Bayesian filter-based algorithm to biometric information obtained in multiple modes (e.g., single mode and array mode) and measurement data associated with an environment (e.g., temperature, humidity, pressure, and inertia) outside the body.

Although the above-mentioned embodiments have been described by limited drawings, those skilled in the art may apply various technical modifications and alterations based on the above embodiments. For example, appropriate results can be achieved although described techniques are carried out in a different order from a described method, and/or described elements are combined or mixed in a different form from the described method, or replaced or substituted with other elements or equivalents.

Therefore, other implementations, other embodiments, and equivalents to patent claims belong to the scope of the patent claims to be described later.

What is claimed is:

1. A biosensor using an array antenna, comprising:
   at least two antenna elements that are spaced apart from each other along the lateral circumference of an object, radiate electromagnetic waves having a directivity toward the inside of the object, and receive a scattered electromagnetic field;
   a signal generator for generating a feed signal with a frequency sweep;
   a phase shifter for adjusting the phase of the feed signal and transmitting the feed signal to the at least two antenna elements; and
   a controller for detecting the location of a target part inside the object based on the scattered electromagnetic field received in response to the electromagnetic waves radiated by sweeping the frequency and phase of the feed signal.

2. The biosensor of claim 1, wherein the controller starts measuring biometric information of the target part, in response to a detection of the location of the target part.

3. The biosensor of claim 1, wherein the controller obtains a frequency response characteristic for the scattered electromagnetic field, calculates a time delay profile from the frequency response characteristic, and determines the location of the target part based on the time delay profile.

4. The biosensor of claim 3, wherein the controller detects a target peak from the time delay profile and determines the location of the target part based on the target peak of the time delay profile.

5. The biosensor of claim 4, wherein the controller maintains a phase difference corresponding to the time delay profile, in response to a second peak as the target peak that has a predetermined amplitude range in a predetermined delay range.

6. The biosensor of claim 3, wherein the controller obtains a frequency response characteristic for each phase difference by sweeping the frequency of the feed signal for each of phase differences that can be selected by the phase shifter.

7. The biosensor of claim 1, wherein the controller determines a direction in which the target part is located with respect to the biosensor.

8. The biosensor of claim 1, wherein, in response to a single-mode operation, one or more of the at least two antenna elements radiate electromagnetic waves and the other antenna elements receive a fringing field by the electromagnetic waves, and, in response to an array-mode operation, both of the at least two antenna elements radiate electromagnetic waves and receive the scattered electromagnetic field.

9. The biosensor of claim 8, wherein the operation time of the single mode is longer than the operation time of the array mode.

10. The biosensor of claim 8, wherein the operation time of the single mode and the operation time of the array mode do not overlap each other.

11. The biosensor of claim 8, wherein the controller determines glucose level data while operating in the single mode and determines time delay-related information of the glucose level data while operating in the array mode.

12. The biosensor of claim 1, wherein a beam pattern of the electromagnetic waves radiated by the at least two antenna elements is determined based on the phase difference adjusted by the phase shifter.

13. The biosensor of claim 1, wherein the at least two antenna elements receive signals radiated from an internal sensor disposed inside the object, and the controller compares the phases of the signals received by the at least two antenna elements to determine whether the internal sensor and the biosensor are in alignment.

14. The biosensor of claim 13, further comprising an output unit that provides the user with guidance information for changing the wearing position of the biosensor in response to a misalignment state of the internal sensor and the biosensor,
   wherein the controller determines an alignment state if the signals received by the at least two antenna elements are in phase and determines the misalignment state if the signals received by the at least two antenna elements are out of phase.

15. The biosensor of claim 1, wherein the at least two antenna elements are disposed along a curved surface corresponding to a curvature on the surface of the object.

* * * * *